US012351856B2

(12) United States Patent
Rozas Andreu et al.

(10) Patent No.: US 12,351,856 B2
(45) Date of Patent: Jul. 8, 2025

(54) METHOD FOR DETECTING OPIOIDS, OPIATES, CANNABINOIDS, OR BENZODIAZEPINES IN A SAMPLE WITH A β-GLUCURONIDASE ENZYME

(71) Applicant: KURA BIOTECH INC., Rancho Dominguez, CA (US)

(72) Inventors: Manuel Rozas Andreu, Puerto Varas (CL); Daniel E. Almonacid Coronado, Lafayette, CA (US)

(73) Assignee: KURA BIOTECH INC., Rancho Dominguez, CA (US)

( * ) Notice: Subject to any disclaimer, the term of this patent is extended or adjusted under 35 U.S.C. 154(b) by 0 days.

(21) Appl. No.: 17/959,215

(22) Filed: Oct. 3, 2022

(65) Prior Publication Data

US 2023/0140113 A1    May 4, 2023

Related U.S. Application Data

(62) Division of application No. 16/673,775, filed on Nov. 4, 2019, now abandoned, which is a division of application No. 15/442,607, filed on Feb. 24, 2017, now abandoned.

(30) Foreign Application Priority Data

Aug. 26, 2016    (GB) ...................................... 1614546

(51) Int. Cl.
*C12Q 1/34* (2006.01)
*G01N 33/569* (2006.01)
*G01N 33/94* (2006.01)
*G01N 30/72* (2006.01)

(52) U.S. Cl.
CPC .......... *C12Q 1/34* (2013.01); *G01N 33/56916* (2013.01); *G01N 33/948* (2013.01); *G01N 33/9486* (2013.01); *G01N 30/72* (2013.01); *G01N 2333/924* (2013.01)

(58) Field of Classification Search
CPC ........... G01N 33/56916; G01N 33/948; G01N 33/9486; G01N 30/72; G01N 2333/924; C12Q 1/34; C12Y 302/01031
See application file for complete search history.

(56) References Cited

U.S. PATENT DOCUMENTS

| | | | |
|---|---|---|---|
| 4,473,640 A | 9/1984 | Combie et al. | |
| 4,495,278 A | 1/1985 | Thomas | |
| 4,642,288 A | 2/1987 | Elia De Miguel et al. | |
| 5,104,794 A | 4/1992 | Kondo et al. | |
| 5,750,381 A | 5/1998 | Scheinmann et al. | |
| 10,508,297 B2 | 12/2019 | Rozas et al. | |
| 2002/0122815 A1 | 9/2002 | Peroutka | |
| 2016/0076075 A1* | 3/2016 | McIntire | C12Q 1/34 435/18 |
| 2016/0090582 A1 | 3/2016 | Lee | |
| 2016/0237415 A1 | 8/2016 | Lee | |
| 2017/0029801 A1 | 2/2017 | Kaneko et al. | |
| 2018/0067116 A1 | 3/2018 | Rozas et al. | |
| 2020/0116719 A1* | 4/2020 | Rozas Andreu | C12Q 1/34 |

FOREIGN PATENT DOCUMENTS

| | | |
|---|---|---|
| WO | 9516050 | 6/1995 |
| WO | 2015156398 A1 | 10/2015 |

OTHER PUBLICATIONS

Jannetto, PJ et al. Pain management in the 21st century: utilization of pharmaceogenomics and therapeutic drug monitoring. Expert Opinion on Drug Metabolism & Toxicology. 2011. 7(6): 745-752. (Year: 2011).*
Stout, PR et al. Journal of Analytical Toxicology. 2010. 34: 430-443. (Year: 2010).*
Declaration Under 37 CFR 1.132 by Manuel Rozas Andreu. Mar. 11, 2022. 3 pages. (Year: 2022).*
Hafstrom, T et al. Complete genome sequence of *Brachyspira intermedia* reveals unique genomic features in *Brachyspira* species and phage-mediated horizontal gene transfer. BMC Genomics. 2011. 12:395. (Year: 2011).*
Result 5 of Seq ID No. 1 search performed on UniProt database. Sequence integrated into UniProtKB/TrEMBL on Oct. 19, 2011. Search performed on Mar. 12, 2023. (Year: 2011).*
Pati, A et al. Complete genome sequence of *Brachyspira murdochii* type strain (56-150T). Standards in Genomic Sciences. 2010. 2: 260-269. (Year: 2010).*
Result 7 of Seq ID No. 1 search performed on UniProt database. Sequence integrated into UniProtKB/TrEMBL on Jul. 13, 2010. Search performed on Mar. 12, 2023. (Year: 2010).*
"Beta-glucuronidases The New Generation, BGTurbo" BGTurbo TM Downloaded Jan. 26, 2017 from http://www.kurabiotec.com/products-2/bgluc-newgeneration/ 1 page. Copyright 2015 Kura Biotec SpA.
Wang, et al., J. Anal. Toxicol. 2006, vol. 30: pp. 570-575.
EBG TM *E. coli* Recombinant β-Glucuronidase Overview and DataSheet Downloaded Jan. 26, 2017 from http://www.kurabiotec.com/products-2/e-coli-%ce%b2-glucuronidase/ Copyright 2015 Kura Biotec SpA.
IMCSzyme TM Product Specifications, 4 pages. Downloaded Jan. 26, 2017 from http://www.imcszyme.com/.
Kemp, et al., "Comparison of Species-Specific β-Glucuronidase Hydrolysis of Cannabinoid Metabolites in Human Urine" FAA 2015 Report No. DOT/FAA/AM-15/6. 18 pages.

(Continued)

*Primary Examiner* — David W Berke-Schlessel
*Assistant Examiner* — Susan E. Fernandez
(74) *Attorney, Agent, or Firm* — Mintz, Levin, Cohn, Ferris, Glovsky & Popeo, P.C.

(57) ABSTRACT

The present invention discloses a highly efficient method for detecting opioids, opiates, cannabinoids, or benzodiazepines present in a sample, comprising the steps of adding to said sample an enzyme with β-glucuronidase activity originated from genus *Brachyspira* or any mutant derived thereof; incubating the sample with the enzyme; and detecting said opioids, opiates, cannabinoids, or benzodiazepines by means of a suitable technique.

7 Claims, 3 Drawing Sheets

Specification includes a Sequence Listing.

(56) References Cited

OTHER PUBLICATIONS

Wakabayashi, et al., J. Biol. Chem. 1961, vol. 236(4): pp. 996-1001.
Boppana, V., et al., "Immobilized Sulfatase:B-Glucuronidase Enzymes for Qualitative and Quantitative Analysis of Drug Conjugates", J. Pharm. Sci., 1989, vol. 78(2): pp. 127-131.
Bayat, M., et al. "A comparative study of structure, stability and function of sc-tenecteplase in the presence of stabilizing osmolytes" Journal of Biotechnology 280, pp. 1-10 (2010). (https://doi.org/10.1016/j.jbiotec.2018.05.014).
Fonin, A.V., et al. "Protein Folding and Stability in the Presence of Osmolytes" Molecular Biophysics, ISSN 0006-3509, Biophysics, vol. 61, No. 2, pp. 185-192 (2016). (https://doi.org/10.1134/S0006350916020056).
Bruzdziak, P., et al. "Influence of Osmolytes on Protein and Water Structure: A Step To Understanding the Mechanism of Protein Stabilization" Journal of Physical Chemistry B 117, pp. 11502-11508 (2012).
Beauchamp, D., et al. "Studying salt effects on protein stability using ribonuclease t1 as a model system" Biophysical Chemistry 161, pp. 29-38 (2012). (https://doi.org/10.1016/j.bpc.2011.11.004).
Feng, S., et al. "Effects of glycerol on the compaction and stability of the wild type and mutated rabbit muscle creatine kinase" Proteins, 71, pp. 844-854 (2007). (https://doi.org/10.1002/prot.21744).
Kraaz, W et al. Brachyspira aalborgi infection diagnosed by culture and 16S ribosomal DNA sequencing using human colonic biopsy speciments, Journal of Clinical Microbiology, 2000, 38(10): 3555-3560, (Year: 2000).
Kura Bietec, "Beta-glucuronidases: The New Generation, BGTurbo," Archived Aug. 16, 2016, Retrieved from Archive.org on Dec. 3, 2018: <URL: https://web.archive.org/web/20160816053619/http://www.kurabiolec.com:80/products/bluc-newgeneration/>, (Year: 2016).
Mappley, LJ et al. Comparative genomics of *Brachyspira pilosicoli* strains: genome rearrangements, reductions and correlalion of genetic compliment with phenotypic diversity, BMC Genomics, 2012, 13: 454, 18 pages, (Year: 2012).
Uniprot, Sequences for J9UK14_BRAPL and KOJGG2_BRAPL, Integrated into UniProlKB/TrEMBL on Nov. 28, 2012, Accessed on Nov. 29, 2018, (Year: 2012).
UniProt Consortium, "UniProt: a hub for protein information," Nucleic Acids Res, 2015, vol. 43, Database issue, pp. D204-D212.
Database Genbank (2012) "Brachyspira Pilosicoli B2904, Complete Genome", Accession No. CP003490.1, 464 pages.
Malik-Wolf et al. (2014) "Evaluation of Abalone B-Glucuronidase Substitution in Current Urine Hydrolysis Procedures", Journal of Analytical Toxicology, 38:171-176.
Morris et al. (2014) "Rapid Enzymatic Hydrolysis Using a Novel Recombinant B-Glucuronidase in Benzodiazepine Urinalysis", Journal of Analytical Toxicology, 38:610-614.

\* cited by examiner

METHOD FOR DETECTING OPIOIDS, OPIATES, CANNABINOIDS, OR BENZODIAZEPINES IN A SAMPLE WITH A β-GLUCURONIDASE ENZYME

CROSS-REFERENCE TO RELATED APPLICATIONS

This application is a Continuation Application of U.S. patent application Ser. No. 16/673,775, filed on Nov. 4, 2019, which is a Divisional Application of U.S. patent application Ser. No. 15/442,607 filed Feb. 24, 2017, which claims priority to GB Patent Application No. 1614546.8, filed on Aug. 26, 2016, the entire contents of which are incorporated herein by reference.

REFERENCE TO AN ELECTRONIC SEQUENCE LISTING

The contents of the electronic sequence listing identified as follows: (SequenceListing_ST26_1268-600_US-DIV_XML.xml; Size: 8,578 bytes; and Date of Creation: Jan. 17, 2023) is herein incorporated by reference in its entirety.

TECHNICAL FIELD

The present invention is related with the technical field of biotechnology, and particularly provides a method for detecting products derived from glucuronide metabolites such as opioids, opiates, cannabinoids, or benzodiazepines present in a sample, using for this purpose a β-glucuronidase enzyme from bacterial origin.

BACKGROUND OF THE INVENTION

Conjugation of endogenous and exogenous compounds with D-glucuronic acid is a metabolic pathway commonly known in animals and humans, which is normally considered as a process for detoxification of organisms. Through this process, glucuronide conjugates or metabolites are produced, which are excreted through urine or bile (Boppana V et al, J. Pharm. Sci. 1989. Vol 78(2):127-131). Compounds that are excreted in these ways are mainly lipophilic, such as bilirubin, androgens, glucocorticoids, among others, and xenobiotic substances such as opioids, cannabinoids, benzodiazepines, among others.

Detection of these glucuronide metabolites in biological fluids allows identification and quantitation of endogenous or exogenous compounds present in the organism. Said detection can be performed by means of chemical hydrolysis (acid hydrolysis) or by means of enzymatic hydrolysis of said glucuronide metabolites. Chemical hydrolysis is performed with an acid which hydrolyses most of conjugates in a relative reduced period of time (from 60 to 90 minutes) and at a low cost. However, the acid conditions and temperature required in this process degradate sensitive compounds, for example, benzodiazepines. Moreover, working with acids in the laboratory requires stricter security conditions, producing corrosion of vulnerable equipment. For this reason, testing laboratories for these purposes mainly employ enzymatic hydrolysis, consisting in the use of β-glucuronidases for hydrolyzation of glucuronide metabolites in conditions more manageable than acid hydrolysis.

Currently there exist diverse β-glucuronidase enzymes available from different origins, each one with optimum conditions for hydrolysis of metabolites. Thus, parameters such as concentration, pH, incubation period and temperature of reaction vary depending on the enzyme used.

For example, there exist alternatives of enzymes obtained from molluscs such as a β-glucuronidase enzyme originated from *Patella vulgata* described in document U.S. Pat. No. 4,473,640 of Combie et al, which requires a temperature between 60 and 70 degrees Celsius, pH 5, and at least one hour to obtain only 60% of hydrolysis of the glucuronide metabolite, and approximately three hours as the optimum time to reach complete quantification of the hydrolyzed metabolite. There also exist β-glucuronidase enzymes described from species *Helix pomatia, Helix aspersa, Haliotis rufescens*, among others (WO 95/16050, Scheinmann et al; Kemp et al, FAA. 2015. Report No. DOT/FAA/AM-15/6). Generally, preparations of enzymes obtained from molluscs tend to have more contaminant substances that may interfere with further analysis of glucuronide metabolites.

On the other hand, there also exist alternatives to enzymes from bacterial origin, such as β-glucuronidase from *Escherichia coli*. Comparative studies show that at an optimum pH and depending on the type of glucuronide metabolite/substrate, it is required an hour of incubation to obtain 40-80% of hydrolysis, and between three to five hours to reach a complete hydrolysis (Wakabashi et al, J Biol. Chem. 1961. Vol 236(4):996-1001). These detection times are excessive for testing laboratories which analyze drugs in biological samples, and the situation is even more dramatic in cases such as analysis of natural opioids (codeine and morphine) and semi-synthetic opioids (hydromorphone, oxycodone and oxymorphone). The hydrolysis percentage of conjugated metabolites of these opioids widely varies depending on the origin of the enzyme used: after an incubation period of two hours of the biological sample with β-glucuronidase from *Patella vulgata*, only a 21% of codeine and a 64% of morphine are recovered; an 11% of codeine and a 35% of morphine are obtained when β-glucuronidase from *Helix pomatia* is used; and only a 9% of codeine and morphine are recovered when β-glucuronidase from *Escherichia coli* is used (Wang et al., J Anal. Toxicol. 2006. Vol 30:570-575). For this reason, diverse researchers seek enzymes capable of reduce the time needed to hydrolyze glucuronide metabolites. The recently published patent application US 2016/0090582 discloses a recombinant β-glucuronidase enzyme from *E. coli* (IMCSzyme™), which, according to the applicant, detects the presence of drugs in biological samples in 30 minutes or less, whose specific activity is three times higher than wild type enzyme. However, in the examples section it is shown that 60 minutes are required to incubate the mutant enzyme with a sample containing codeine-6-glucuronide at 55 degrees Celsius to recover 93.5% of codeine.

Therefore, new β-glucuronidase enzymes are needed to achieve quick hydrolysis of glucuronide metabolites and to obtain high recovery percentages of their derivatives, in order to implement a highly efficient method for detection and quantification of the same.

SUMMARY OF INVENTION

The present invention discloses a method for detecting opioids, opiates, cannabinoids, or benzodiazepines in a sample, comprising the steps of:
  a) providing the sample in which said opioids, opiates, cannabinoids, or benzodiazepines are to be detected;
  b) adding to said sample an enzyme with β-glucuronidase activity originated from genus *Brachyspira* or any mutant derived thereof;

c) incubating the sample with the enzyme; and
d) detecting said opioids, opiates, cannabinoids, or benzodiazepines through any suitable technique.

In a preferred embodiment, the sample from which said opioids, opiates, cannabinoids, or benzodiazepines are to be detected, is a biological sample preferably selected from the group consisting of saliva, whole blood, plasma, urine, hair, skin, teeth, soft tissues, meconium, vitreous humor, water and food.

The enzyme with β-glucuronidase activity of the present invention, preferably originates from species *Brachyspira pilosicoli*. In a preferred embodiment, the β-glucuronidase enzyme has the amino acid sequence shown in SEQ ID NO:1. The invention also includes any mutant enzyme derived from SEQ ID NO:1 that maintains its β-glucuronidase activity. Preferably, the mutant enzyme with β-glucuronidase activity shares at least an 80% of identity with the sequence defined in SEQ ID NO:1.

In another preferred modality of the method of the present invention, the step of incubating the sample with the enzyme is performed in a period of at least one minute, preferably between 2 and 120 minutes, and even more preferably between 3 and 30 minutes. Preferably, said incubation is performed in a range of temperature between 20 and 60 degrees Celsius, preferably between 50 and 55 degrees Celsius, and in a pH range between 4.0 and 9.0, preferably between 6.5 and 7.5.

The detection of opioids, opiates, cannabinoids, or benzodiazepines is performed through any suitable analytical technique, preferably selected from the group consisting of liquid chromatography (LC) or gas chromatography (GC), high performance liquid chromatography (HPLC), followed by mass spectrometry (LC-MS, or GC-MS), or high resolution mass spectrometry (LC-HRMS, HPLC-HRMS), or tandem mass spectrometry (LC-MS-MS, GC-MS-MS, HPLC-MS-MS) or any other suitable technique or combination of detection methods.

DETAILED DESCRIPTION OF THE INVENTION

The present invention relates to a method for detecting products derived from glucuronide metabolites, preferably opioids, opiates, cannabinoids, or benzodiazepines present in a sample, comprising the use of a new β-glucuronidase enzyme originated from *Brachyspira* genus. Hydrolysis efficiency of said enzyme is widely superior than all β-glucuronidases currently known, with a specific activity 6.6 times higher than mean specific activity of a β-glucuronidase obtained from *E. coli*. This allows to detect products derived from glucuronide metabolites in less than 15 minutes with a high recovery rate.

All the technical and scientific terms used to describe the present invention have the same meaning understood by any person with basic knowledge in the field under review. Nevertheless, to define more clearly the scope of the invention, a list of terminology used in this description is given below.

It should be understood that as used herein, the term "glucuronide metabolite" refers to any compound conjugated with glucuronic acid through a glycosidic bond. It is to be understood that a glucuronide metabolite can be natural or synthetic, and produced by chemical or enzymatic methods. The terms "conjugated compound", "conjugated metabolite", "glucuronide compound", and "glucuronide substrate" are indistinctly used to describe the technical characteristics of the present invention.

The term "products derived from glucuronide metabolites" or "recovered analytes" should be understood as the molecule or original compound that is produced after hydrolysis or glycosidic bond cleavage of a glucuronide metabolite. These derived products or original compounds can be natural or synthetic, and produced by chemical or enzymatic methods.

The term "enzyme" should be understood as a sequence of amino acids which form a functional protein of interest for the present invention. It is to be understood that the present invention is not related with enzymes in their natural state, but it relates to proteins in an isolated state, purified or partially purified, or recombinant, obtained by any method of genetic engineering known in the state of the art. Likewise, it is to be understood that the term "mutant" or "mutant enzyme" refers to a modified protein derived from the original amino acid sequence maintaining its β-glucuronidase enzymatic activity; and sharing at least 70%, preferably 80% and more preferably 90% of identity with the original sequence.

It is to be understood that the term "identity" among amino acid sequences refers to the percent of identical amino acids that the compared sequences share among them, in a particular sequence alignment window. The percentage of identity can be calculated using a sequence comparison algorithm or by manual alignment together with visual inspection. For example, sequences and percentages of identity can be obtained using computer resources available on internet such as BLAST (blast.ncbi.nlm.nih.gov) or FastDB computer programs.

The term "Unit (U)" should be understood as the unit used to measure the specific activity of an enzyme. One unit will produce 1.0 µg of phenolphthalein from phenolphthalein glucuronide (PPG) metabolite per hour at 37 degrees Celsius at pH 6.8.

The term "vehicle" should be understood as any substance that is added to an active principle, in this case an enzyme, which is useful as a support and allows to dilute or improve stability or durability of the main compound.

As described before, an object of the present invention relates to a method for detection of glucuronide metabolites in a sample, which comprises the steps of adding an enzyme with β-glucuronidase activity from genus *Brachyspira* or any variant or mutant derived thereof to the sample in which a product derived from a glucuronide metabolite is to be detected, incubating the sample with the enzyme for a determined period of time; and detecting the product derived from said glucuronide metabolite through any suitable technique.

This method is superior than others described in the state of the art, since it includes the use of the new enzyme with β-glucuronidase activity originated from genus *Brachyspira*, which has an improved affinity for glucuronide metabolites, a specific activity 6.6 times higher than β-glucuronidase originated from *E. coli*, and therefore it is capable of hydrolyse glucuronide metabolites to be detected in a period of time of at least one minute, preferably between three and 30 minutes. This enzyme is preferably originated from species *Brachyspira pilosicoli*, whose amino acid sequence is shown in SEQ ID NO:1, but it can be obtained from any species of genus *Brachyspira*. Additionally, in the method of the present invention, any derivative or mutant of this protein can be used, provided that it maintains its β-glucuronidase activity. Preferably, the derived or mutant enzyme with β-glucuronidase activity shares at least a 70% of sequence identity, more preferably an 80% of identity, and even more preferably a 90% of identity with the sequence defined in SEQ ID NO:1.

The β-glucuronidase enzyme originated from *Brachyspira* can hydrolyse any glucuronide metabolite, whether from natural, semi-synthetic or synthetic origin. Some examples of these metabolites, without limitation, are: morphine-3-morphine-6-glucuronide, codeine-6-glucuronide, oximorphone-glucuronide, glucuronide, hydromorphone-glucuronide, norbuprenorphine-glucuronide, buprenorphine-glucuronide, oxazepam-glucuronide, temazepam-glucuronide, lorazepam-glucuronide, alprazolam-glucuronide, midazolam-glucuronide, nordiazepam-glucuronide, psilocin-glucuronide, carboxy-tetrahydrocannabinol-glucuronide, tetrahydrocannabinol-glucuronide, tetrahydrocannabinolic acid-glucuronide, naloxone-3-glucuronide, tapentadol-glucuronide, tricyclic antidepressant-glucuronide, cannabidiol-glucuronide, among others. It is to be understood for the scope of the present invention that the β-glucuronidase enzyme originated from *Brachyspira* can hydrolise any glucuronide metabolite and it is not limited to the examples previously mentioned.

Therefore, this method allows to detect any product derived from glucuronide metabolites, whether from natural, semi-synthetic or synthetic origin. For example, the method can be used to analyze drugs, toxic compounds derived from fungi, androgens, estrogens, mineralocorticoids, glucocorticoids, fatty acid derivatives, retinoids, among others.

In a preferred embodiment, products derived from glucuronide metabolites are selected from the group consisting of opioids, opiates, cannabinoids, benzodiazepines or any other derived thereof. Preferably, the products derived from glucuronide metabolites are selected from the group consisting of morphine, codeine, oximorphone, hydromorphone, norbuprenorphine, buprenorphine, oxazepam, temazepam, lorazepam, alprazolam, midazolam, nordiazepam, psilocin, 11-nor-9-carboxy-tetrahydrocannabinol (THC-COOH), tetrahydrocannabinol (THC), tetrahydrocannabinolic acid (THCa), naloxone, tapentadol, tricyclic antidepressant, cannabidiol, among others, without being limited to the examples described herein.

In a preferred embodiment of the present invention, the method allows to detect any product derived from glucuronide metabolites in any type of sample, which is preferably selected from the group consisting of saliva, whole blood, plasma, urine, hair, skin, teeth, soft tissues, water, food, meconium and vitreous humor, without restriction to these types of samples. The following biological samples can also be used: bile, earwax, phlegm, vomit, aqueous humour, tears, amniotic fluid, vaginal secretion, semen, pre-ejaculate fluid, mucus, sebum, sweat, excrement, or any other suitable sample without limitation to the animal fluids previously mentioned. Other suitable samples originate from a non-animal source, such as food, water or chemical solutions from laboratories.

In the method of the present invention, β-glucuronidase enzyme originated from genus *Brachyspira* is added to the sample and the mixture is incubated for a determined period of time, in suitable conditions. In a preferred embodiment, incubation period of sample with the enzyme is of at least one minute, that is to say, only one minute of reaction is enough to detect the presence of a product derived of a glucuronide metabolite in a sample. However, incubation period can be extended to 16 hours or even more, provided that time is not an impediment to the technician performing the method.

More preferably, incubation period is between 2 and 120 minutes, and even more preferably, incubation period is between 3 and 30 minutes, since obtaining the results efficiently and in the shortest time is commonly desired. Additionally, adequate incubation conditions refer to ideal conditions of temperature and pH in order to allow the reaction to be produced in the time periods mentioned. Regarding temperature, incubation is performed preferably in a range between 20 and 60 degrees Celsius, and even more preferably in a range of 50 to 55 degrees Celsius. Regarding pH, incubation is performed in a range between 4.0 and 9.0 and preferably between 6.5 and 7.5. As part of the elements routinely used in these assays, incubation is performed in presence of buffer solutions, standards of products derived from glucuronide metabolites, polar or apolar solvents, among others.

After incubating the β-glucuronidase enzyme with the sample and before separating the products derived from glucuronide metabolites through separation columns, an extraction step of said metabolites can be optionally included to increase sensitivity of analytical techniques. This extraction step can be performed by means of liquid-liquid extraction (LLE), solid-liquid extraction (SLE), extraction in solid phase (SPE), or any other suitable technique. However, the step of extracting the products derived from glucuronide metabolites adds a laborious step to the analytical method and increases operational costs due to the use of solvents and other materials.

To the method of the present invention, the latter step is optional due to the availability of highly selective analytical techniques that allow direct analysis by means of the technique named "dilute and shoot", which consist of diluting the sample with an adequate solution and injecting it directly into a separation column. Moreover, the method does not require elimination of the enzyme since the β-glucuronidase of the present invention is highly purified and has a high reactivity; and therefore, a small volume of the enzyme is required to react with glucuronide metabolites. In a preferred embodiment the volume range of enzyme: liquid sample used, for example, urine, is from 1:1 to 1:14. Preferably, optimum concentration is between 0.02 and 0.25 mg of enzyme per mL of total reaction. In this manner, the volume of enzyme used does not affect or damage the separation column in case it is directly injected to it. The adequate solvent can be for example, water or a mixture of water with methanol, or any mixture of solvents that can be used to dilute the sample.

Finally, detection of products derived from glucuronide metabolites is performed through the use of separation columns and analytical techniques which are selected from the group consisting of: gas chromatography (GC), liquid chromatography (LC) or high performance liquid chromatography (HPLC), solid phase microextraction (SPME), with mass spectrometry detectors (GC-MS; LC-MS; HPLC-MS; SPME-MS), high resolution mass spectrometry (GC-HRMS; LC-HRMS; HPLC-HRMS), tandem mass spectrometry (GC-MS/MS; LC-MS/MS; SPME-GC-MS/MS), time of flight mass spectrometry (LC-TOF-MS), ultraviolet-visible spectrophotometry (GC-UV/Vis; LC-UV/Vis; SPME-LC-UV/Vis), flame ionization detection (GC-FID; LC-FID; SPME-GC-FID), photodiode array detection, (LC-DAD), or any other suitable detection method, without limiting to the examples previously mentioned.

A second object of the present invention is a reagent for detection of products derived from glucuronide metabolites in a sample, which comprises an enzyme with β-glucuronidase activity originated from genus *Brachyspira* or any derived enzyme or mutant thereof; which is included in a suitable vehicle.

Preferably, the reagent contains an enzyme with β-glucuronidase activity originated from species *Brachyspira pilosicoli*, or any derived enzyme or mutant thereof. Said enzyme has an amino acid sequence shown in SEQ ID NO:1, but it can be any enzyme mutant from said sequence and maintaining β-glucuronidase activity. Preferably, the derived or mutant enzyme with β-glucuronidase activity shares at least a 70% or 80% of identity with the sequence defined in SEQ ID NO:1, more preferably a 90% of identity with the sequence defined in SEQ ID NO:1.

In a preferred embodiment, the reagent contains between 0.1 and 2 mg/mL of enzyme, in which the same has a β-glucuronidase activity from 200,000 U/mL to 800.000 U/mL. In addition to β-glucuronidase enzyme, the reagent includes an appropriate vehicle that varies depending on the product format and on the function that the same performs. For example, the reagent including the enzyme can be in a liquid format, which could require only water as a vehicle.

To improve the stability of the enzyme, salts can be added (at concentrations μM or mM), or ethylenediamine tetraacetic acid (EDTA), Tris, dithiothreitol (DTT), hydroxyethylpiperazin-ylethanesulfonic acid (HEPES), citric acid, among others, or a combination thereof. Preferably, salts are selected from the group consisting of sodium phosphate, potassium phosphate, sodium carbonate, sodium acetate, sodium citrate, sodium chloride and potassium chloride, without limitation to the salts previously described. In case that the reagent is frozen, the vehicle to be used can include glycerol, preferably at a concentration of 50%. On the other hand, if the reagent format is powder, which can be produced by means of lyophilisation, spray drying or any other pulverization method; vehicles able to protect the enzyme from drying process are required such as sugars, amino acids and some salts, which are present at a concentration range between 0.001 to 2% based on liquid previous to the drying process. In this case, sugars are preferably selected from the group consisting of sorbitol, trehalose, sucrose, glucose, lactose, mannitol and raffinose, without limitation to these described examples. Therefore, the vehicle of the present invention fulfils the purpose of being a diluting, preservating or stabilizating medium for the enzyme.

The following examples are considered to illustrate the invention and its preferred embodiments, but they must not be considered under any circumstance as a restriction to the scope of the invention, which is defined by the claims attached hereto.

EXAMPLES

Example 1: Synthesis and Expression of β-Glucuronidase Enzyme from *B. pilosicoli*

To express the β-glucuronidase enzyme, nucleotide sequence from said protein was used, originated from *Brachyspira pilosicoli* strain B2904 described in Genbank (access code CP003490), which is shown in SEQ ID NO:2, and codon optimization was performed using the algorithm OptimumGene™ (GenScript) to efficiently express said sequence in *E. coli*. To do this, codon adaptation index (CAI), understood as distribution of frequency of codon usage through the sequence, was adjusted from 0.66 to 0.88, in which a CAI value of 1.0 is considered to be perfect in the desired expression organism; and a CAI value greater than 0.8 is regarded as good in terms of high gene expression levels. Guanine-cytosine content was also optimized to extend mRNA half-life and stem-loop structures were eliminated, since they disrupt ribosome binding and mRNA stability. Optimized nucleotide sequence obtained is shown in SEQ ID NO:3. Amino acid sequence of the enzyme is shown in SEQ ID NO:1.

Figure 1:
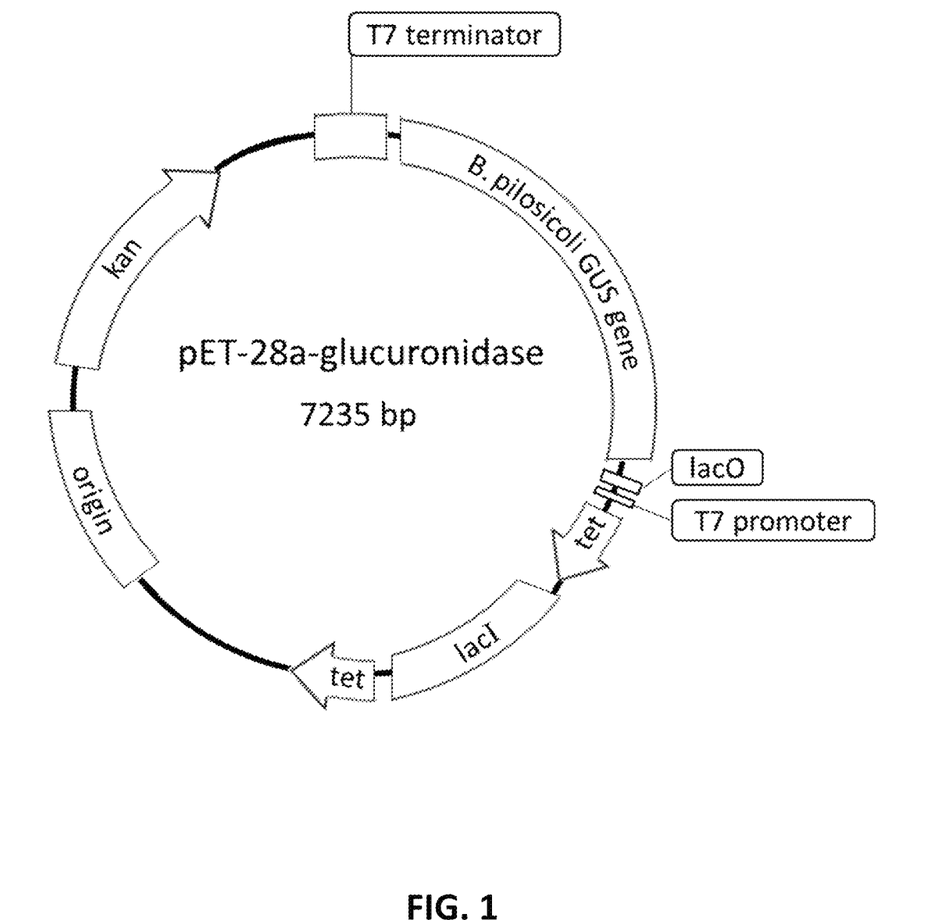
FIG. 1 shows vector pET-28a with the optimized nucleotide sequence encoding β-glucuronidase enzyme originated from *B. pilosicoli* to be expressed in *E. coli*.

The optimized nucleotide sequence of the enzyme was cloned into vector pET-28a, thus vector pET-28a-glucuronidase was obtained, which is shown in FIG. 1. To express β-glucuronidase enzyme from *B. pilosicoli* in *E. coli*, the following protocol was carried out: 5 μL of competent *E. coli* strain BL21 cells were incubated in ice with 10 ng of pET-28a-glucuronidase vector during 20 minutes. Then, bacterial cells were submitted to heatshock at 37 degrees Celsius during 3 minutes. Bacterial cells were then put in ice for 30 seconds and later cells were recovered with 250 μL of LB medium at 37 degrees Celsius and plated in LB-agar with 50 mg/L of kanamycin, and colonies were grown. Finally, a β-glucuronidase activity test was carried out on plates with IPTG (isopropyl-β-thiogalactoside) and X-Gal (5-bromo-4-chloro-3 indolyl-beta-D-thiogalactopyranoside).

In order to purify the enzyme, *E. coli* BL21 transformed cells were grown in 500 mL of LB medium supplemented with kanamycin (50 mg/L), until obtention of an optical density of 0.3, measured using a spectrophotometer at 600 nm ($DO_{600}$).

Then, IPTG at a concentration of 1 mM was added to the culture and then incubated at 37 degrees Celsius during 6 hours. Cells were subjected to sonication during 3 minutes with an amplitude of 60 (cycles of 15 seconds in ice). Later, the enzyme was purified by means of a system for protein purification in columns with Ni-NTA (Nickel-Nitriloacetic acid) resins with elution of 2 mL of Tris-HCl 50 mM, pH 5.6 with imidazole 100 mM pH 5.9 or with imidazole 500 mM pH 4.5.

Figure 2:
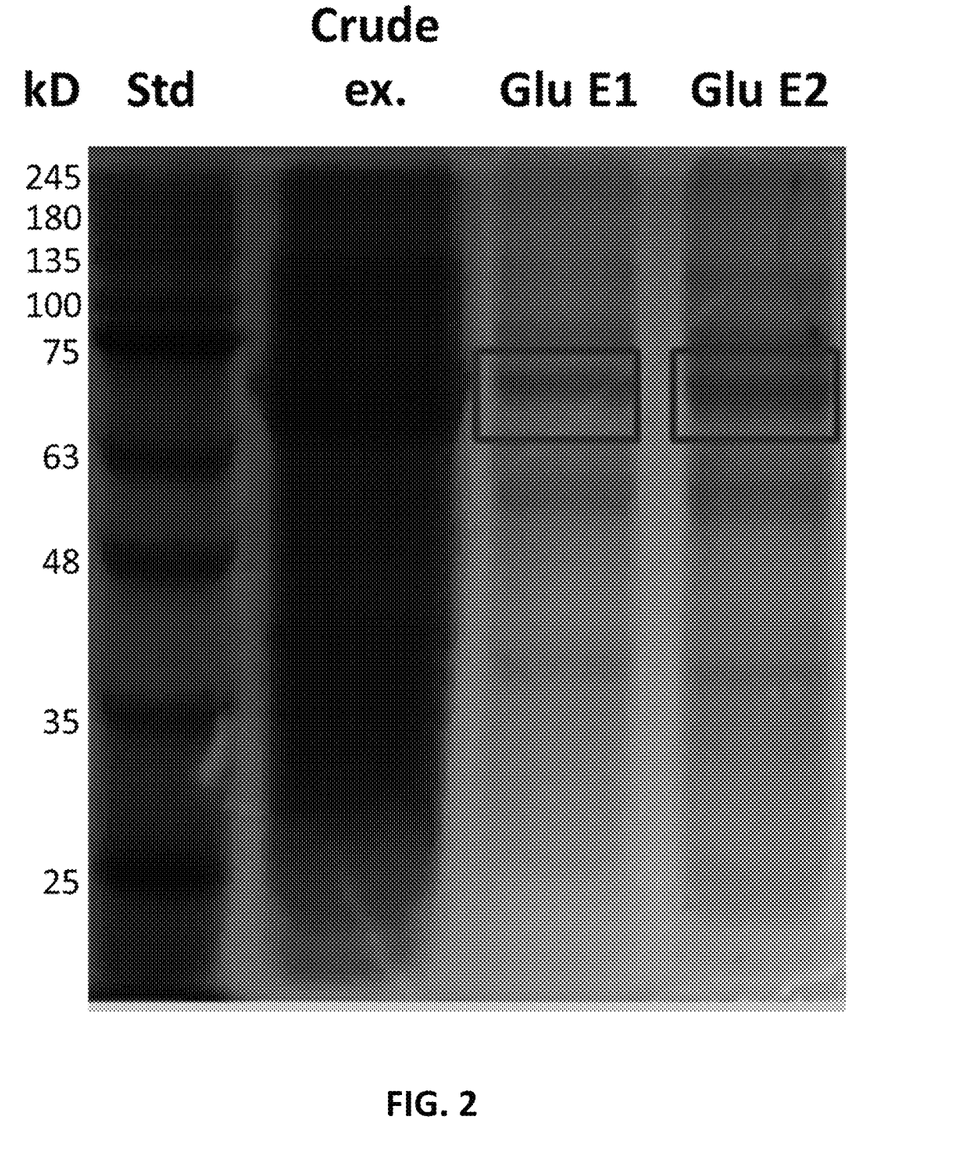
FIG. 2 shows an SDS-PAGE gel of β-glucuronidase enzyme purified with column Ni-NTA.

FIG. 2 shows an SDS-PAGE gel of purified proteins in column Ni-NTA. Each well contained proteins at a concentration of 15 μg/mL, except in crude extract (*E. coli* pET28a-glucuronidase without purification in the column), in which 5 μL were loaded. The acronym Std corresponds to molecular weight standard in kilodaltons (kD), Crude ex corresponds to crude extract, Glu E1 corresponds to elution with imidazole 100 mM pH 5.9 and Glu E2 corresponds to elution with imidazole 500 mM pH 4.5.

Example 2. Incubation Time of a Sample with β-Glucuronidase from *B. pilosicoli*

The required time to hydrolyze morphine-3-glucuronide and codeine-6-glucuronide with the enzyme β-glucuronidase in excess (SEQ ID NO:1) from *B. pilosicoli* was evaluated with the following protocol: 10 μL of glucuronide metabolites at a concentration of 100 μg/mL, free standards (free codeine and morphine calibrators at concentrations of 312.5, 625, 1,000, 1,250 and 1,875 ng/mL), and internal standards (40 μL of deuterated free drug at a concentration of 1 μg/mL to each sample) were added to a sample of 0.4 mL of blank urine and then submitted to vortex agitation. Then, 360 μL of sodium phosphate (pH 7; 140 mM) solution was added to each sample. Then, 240 μL of β-glucuronidase (SEQ ID NO:1) were added to each sample and then agitated by vortex. Samples were incubated at 55 degrees Celsius in an oven during 0, 10, 20, 30, 40, 50 and 60 minutes. A total of 21 samples were used: 7 points of measure at different times, each one in triplicate. Calibrators were incubated for 30 minutes. The samples incubated at different times were removed from oven and the reaction was stopped by adding 700 μL of sodium phosphate buffer solution 1.5 M and agitated by vortex. Then, pH 8-9 was verified with pH paper, and 2 mL of chloroform:isopropanol 50:50 were added to samples, and they were agitated by vortex for 2 minutes. Aqueous phase was discarded, and organic phase was transferred to 12×75 mm assay tubes and then evaporated under nitrogen gas (in a water bath at 50 degrees Celsius) until approximately 1 mL. Samples were then agitated by vortex previous to evaporation until dryness. Samples were reconstituted in 1 mL of HCl 0.5 N in methanol for LC-MS/MS analysis.

Calculation of concentration of equivalents was performed as follows:

Morphine:
Molecular weight of morphine: 285.34 g/mol
Molecular weight of morphine-3-glucuronide: 461.462 g/mol
Proportion of molecular weight of morphine/morphine-3-glucuronide:
Morphine Equivalents:

$$0.6183 \times 2,500 \frac{ng}{mL} \text{ Morphine} - 3 - \text{glucuronide} = 1,545.8 \frac{ng}{mL} \text{ Morphine}$$

Codeine:
Molecular weight of codeine: 299.364 g/mol
Molecular weight of codeine-6-glucuronide: 475.49 g/mol
Proportion of molecular weight of codeine/codeine-6-glucuronide:
Codeine Equivalents:

$$0.62959 \times 2,500 \frac{ng}{mL} \text{ Codeine} - 6 - \text{glucuronide} = 1,574.0 \frac{ng}{mL} \text{ Codeine}$$

Figure 3:
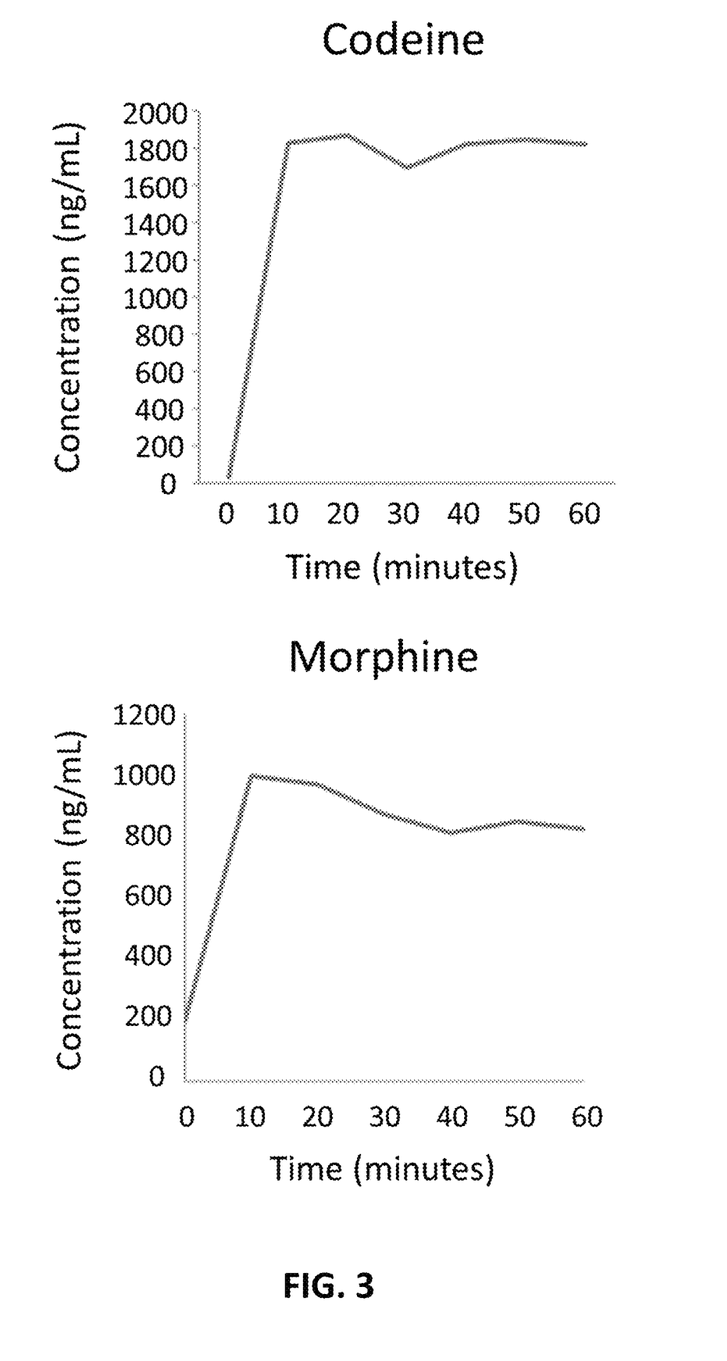
FIG. 3 shows recovery of codeine and morphine versus time, using β-glucuronidase from *B. pilosicoli*.

Table 1 and FIG. 3 show the results obtained. Hydrolysis of 100% of codeine-6-glucuronide was obtained in less than 10 minutes. In the case of morphine, approximately 65% of hydrolysis was obtained within 10 minutes, but these values can be improved by optimizing parameters of temperature, pH or the method to stop reaction. Due to the use of internal controls for recovery of products derived from glucuronide metabolites, values have a standard deviation up to 20%.

TABLE 1

Tabulated results of FIG. 3.

| Time (minutes) | Codeine (ng/mL) | % Yield Codeine | Morphine (ng/mL) | % Yield Morphine |
|---|---|---|---|---|
| 0 | 30.0 | 1.9 | 195.8 | 12.7 |
| 10 | 1826.9 | 116.1 | 997.4 | 64.5 |
| 20 | 1867.5 | 118.6 | 969.2 | 62.7 |
| 30 | 1694.3 | 107.6 | 871.2 | 56.4 |
| 40 | 1821.0 | 115.7 | 811.5 | 52.5 |
| 50 | 1844.3 | 117.2 | 847.4 | 54.8 |
| 60 | 1819.5 | 115.6 | 823.4 | 53.3 |

Example 3: Calculation of Specific Activity of 3-Glucuronidase from *B. pilosicoli*

Specific activity of the β-glucuronidase enzyme from *B. pilosicoli* (SEQ ID NO:1) was calculated and compared with a mean value of three calculations of the specific activity of β-glucuronidase from *E. coli*, using the following protocol: 350 μL of sodium phosphate buffer solution (NaH$_2$PO$_4$) 0.1 M, pH 6.8 were mixed with 350 μL of phenolphthalein β-D-glucuronide sodium salt (0.64 mg/mL) and the mixture was incubated at 37 degrees Celsius. Then, 50 μL of solution containing the enzyme were added to the mixture and incubated at 37 degrees Celsius during 30 minutes. After the first 15 minutes the mixture was gently agitated and stopped at 30 minutes from the beginning of the reaction with 2.5 mL of a glycine solution 0.2 M, pH 10.4. Absorbance was read at 540 nm and the amount of enzyme used was calculated (U/mL) when adjusting the values in a calibration curve. Protein concentration was measured using Bradford method, as widely known in literature. As shown in Table 2, results indicate that SEQ ID NO:1 enzyme has a specific activity 6.6 times higher than mean specific activity of β-glucuronidase from *E. coli*.

TABLE 2

Enzymatic activity of β-glucuronidase from *B. pilosicoli*.

| Enzyme | Activity (U/mL) | Proteins (mg/mL) | Specific Activity (U/mg) |
|---|---|---|---|
| SEQ ID NO: 1 | 427,805 | 2.08 | 205,676 |
| *E. coli* 1 | 68,779 | 2.28 | 30,166 |
| *E. coli* 2 | 102,710 | 3.17 | 32,401 |
| *E. coli* 3 | 85,084 | 2.89 | 29,441 |
| *E. coli* mean value | | | 30,669 |

Example 4. Comparison of β-Glucuronidase from *B. pilosicoli* with β-Glucuronidases from Different Sources To test the efficiency of β-glucuronidase from *B. pilosicoli* (SEQ ID NO:1), this enzyme was compared with two β-glucuronidases currently available in the market: DR2102 (Campbell Science) and BG100™ (KURA Biotec). To do this, 300 ng of each of the glucuronide metabolites of buprenorphine, codeine, hydromorphone, lorazepam, morphine, oxymorphone and 11-nor-9-carboxy-tetrahydrocannabinol (THC-COOH) were added to a sample of blank urine, therefore obtaining spiked urine. Each enzyme was used under the conditions proposed by each manufacturer. Hydrolysis of 50 μL of urine was performed, diluting it with 250 μL of buffer solution at pH 6.8, 20 μL of internal standards (ISTD) and 10 μL of DR2102 or BG100 enzymes, or 20 μL of SEQ ID NO:1. Incubation conditions are shown in Table 3.

TABLE 3

Conditions used for each enzyme.

| Conditions | DR2102 | BG100 ™ | SEQ ID NO: 1 |
|---|---|---|---|
| Urine (μL) | 50 | 50 | 50 |
| ISTD (μL) | 20 | 20 | 20 |
| Buffer (μL) | 25 | 25 | 25 |
| Enzyme (μL) | 10 | 10 | 20 |
| Temperature (° C.) | 62 | 68 | 50 |
| Time (minutes) | 60 | 30 | 15 |

After hydrolysis, samples were centrifuged at 24,000 g, diluted with 450 μL of a solution comprising 95% water and 5% methanol, and charged to an HPLC column (Phenomenex). Protein amount in samples was measured before and after centrifugation at 24,000 g using a NanoDrop spectrophotometer (Thermo Scientific). As a result, the reactions performed were carried out with 1.787 mg/ml of DR2102, 0.554 mg/ml of BG100™ and 0.103 mg/ml of SEQ ID NO:1 enzyme.

Recovery yields of products derived from glucuronide metabolites are shown in Table 4. As shown, mean recovery of derived products was improved in a 15% when hydrolysis was performed with SEQ ID NO:1 enzyme in only 15 minutes and using 70% and 94% less of protein amount in comparison to the other two enzymes. It is interesting to mention that β-glucuronidase enzyme from *B. pilosicoli* is more reactive with codeine-6-glucuronide than the other enzymes.

TABLE 4

Results of analites recovered from hydrolysis of glucuronide metabolites with three β-glucuronidases enzymes from different origins.

| Recovered Analyte | DR2102 60 minutes (ng/mL) | BG100 ™ 30 minutes (ng/mL) | SEQ ID NO: 1 15 minutes (ng/mL) |
|---|---|---|---|
| Buprenorphine | 223.1 | 271.1 | 224.4 |
| Codeine | 159.4 | 173.8 | 243.2 |
| Hydromorphone | 176.8 | 196.0 | 196.2 |
| Lorazepam | 214.9 | 202.5 | 185.9 |
| Morphine | 174.5 | 190.9 | 198.1 |
| Oximorphone | 155.8 | 189.0 | 169.4 |
| THC-COOH | 75.5 | 146.0 | 140.6 |
| Protein in sample pre-centrifugation | 1.787 (mg/mL) | 0.554 (mg/mL) | 0.103 (mg/mL) |
| Protein in sample post-centrifugation and injected on HPLC column | 0.725 (mg/mL) | 0.280 (mg/mL) | 0.085 (mg/mL) |

Example 5. Comparison of β-Glucuronidase from *B. pilosicoli* with Other β-Glucuronidases from Bacterial Origin In order to test enzyme speed of β-glucuronidase from *B. pilosicoli* (SEQ ID NO:1) in comparison with β-glucuronidases from bacterial origin, SEQ ID NO:1 enzyme was compared with EBG enzyme (recombinant β-glucuronidase from *E. coli*, KURA Biotec) and with IMCSzyme™ (Integrated Micro-Chromatography Systems) at different incubation periods and concentration. The method previously described was used but analyzing only hydrolysis of codeine-6-glucuronide and morphine-3-glucuronide with the conditions described in Table 5.

TABLE 5

Conditions used for each enzyme.

| Conditions | SEQ ID NO: 1 | | | | EBG | IMCSzyme ™ | Control |
| | A | B | C | D | F | — | E |
|---|---|---|---|---|---|---|---|
| Buffer (µL) | 360 | 360 | 360 | 360 | 360 | 360 | 360 |
| Water (µL) | 0 | 120 | 180 | 210 | 180 | 180 | 120 |
| Spiked urine (µL) | 400 | 400 | 400 | 400 | 400 | 400 | 400 |
| Enzyme (µL) | 240 | 120 | 60 | 30 | 60 | 60 | 0 |
| Internal Standard (µL) | 40 | 40 | 40 | 40 | 40 | 40 | 40 |
| Storage buffer control (µL) | 0 | 0 | 0 | 0 | 0 | 0 | 120 |
| Total Volume (µL) | 1,040 | 1,040 | 1,040 | 1,040 | 1,040 | 1,040 | 1,040 |
| Incubation Time (minutes) | 10 | 10 | 10 | 10 | 0, 10, 20 | 0, 10, 20 | 10 |
| pH | 7.0 | 7.0 | 7.0 | 7.0 | 7.0 | 7.0 | 7.0 |
| Temperature (° C.) | 55 | 55 | 55 | 55 | 55 | 55 | 55 |

Each condition shown in Table 5 was assayed in duplicate, and each analysis was measured in triplicate. Calculation of concentration of equivalents was performed as described in Example 2.

Table 6 shows the results obtained from analysis of codeine, and Table 7 shows results obtained from analysis of morphine. As can be noticed, codeine-6-glucuronide was hydrolyzed in a mean value of 109.59% within 10 minutes, using 240 µL of SEQ ID NO:1 enzyme. The value mentioned is greater than 100% because standards of glucuronide metabolites used in the analysis are not completely pure and present a fraction of the original compound that is added to the final result. On the other hand, when comparing hydrolysis yield of codeine-6-glucuronide and morphine-3-glucuronide using the same volume of the enzymes (60 µL), it is shown that SEQ ID NO:1 enzyme is better than the other EBG and IMCSzyme™ enzymes within 10 minutes. Even after an incubation period of 20 minutes of the samples with EBG and IMCSzyme™, these enzymes could not produce the same hydrolysis yield that was obtained with SEQ ID NO:1 enzyme within 10 minutes.

TABLE 6

Results of codeine analysis.

| Condition/Assay | Sample | Codeine (ng/mL) | Codeine % Yield | Average of Assay Yield (%) |
|---|---|---|---|---|
| A/1 | SEQ ID NO: 1 (10 min, 240 µL) | 1,740 | 110.55 | 109.59 |
| A/2 | SEQ ID NO: 1 (10 min, 240 µL) | 1,710 | 108.64 | |
| B/1 | SEQ ID NO: 1 (10 min, 120 µL) | 1,270 | 80.69 | 78.14 |
| B/2 | SEQ ID NO: 1 (10 min, 120 µL) | 1,190 | 75.60 | |
| C/1 | SEQ ID NO: 1 (10 min, 60 µL) | 879 | 55.84 | 54.19 |
| C/2 | SEQ ID NO: 1 (10 min, 60 µL) | 827 | 52.54 | |
| D/1 | SEQ ID NO: 1 (10 min, 30 µL) | 230 | 14.61 | 22.20 |
| D/2 | SEQ ID NO: 1 (10 min, 30 µL) | 469 | 29.80 | |
| F/1 | EBG (0 min, 60 µL) | No Peak | 0.00 | 0.00 |
| F/2 | EBG (0 min, 60 µL) | No Peak | 0.00 | |
| F/1 | EBG (10 min, 60 µL) | 154 | 9.78 | 10.48 |
| F/2 | EBG (10 min, 60 µL) | 176 | 11.18 | |
| F/1 | EBG (20 min, 60 µL) | 396 | 25.16 | 27.10 |
| F/2 | EBG (20 min, 60 µL) | 457 | 29.03 | |
| 1 | IMCSzyme ™ (0 min, 60 µL) | No Peak | 0.00 | 0.00 |
| 2 | IMCSzyme ™ (0 min, 60 µL) | No Peak | 0.00 | |
| 1 | IMCSzyme ™ (10 min, 60 µL) | 189 | 12.01 | 11.85 |
| 2 | IMCSzyme ™ (10 min, 60 µL) | 184 | 11.69 | |
| 1 | IMCSzyme ™ (20 min, 60 µL) | 395 | 25.10 | 27.26 |
| 2 | IMCSzyme ™ (20 min, 60 µL) | 463 | 29.42 | |
| E/1 | Control (10 min) | No Peak | 0.00 | 0.00 |
| E/2 | Control (10 min) | No Peak | 0.00 | |

TABLE 7

Results of the morphine analysis.

| Condition/Assay | Sample | Morphine (ng/mL) | Morphine % Yield | Average of Assay Yield (%) |
|---|---|---|---|---|
| A/1 | SEQ ID NO: 1 (10 min, 240 µL) | 796 | 51.49 | 51.49 |
| A/2 | SEQ ID NO: 1 (10 min, 240 µL) | 796 | 51.49 | |
| B/1 | SEQ ID NO: 1 (10 min, 120 µL) | 717 | 46.38 | 46.90 |
| B/2 | SEQ ID NO: 1 (10 min, 120 µL) | 733 | 47.42 | |
| C/1 | SEQ ID NO: 1 (10 min, 60 µL) | 687 | 44.44 | 43.70 |
| C/2 | SEQ ID NO: 1 (10 min, 60 µL) | 664 | 42.96 | |
| D/1 | SEQ ID NO: 1 (10 min, 30 µL) | 498 | 32.22 | 38.46 |
| D/2 | SEQ ID NO: 1 (10 min, 30 µL) | 691 | 44.70 | |
| F/1 | EBG (0 min, 60 µL) | 179 | 11.58 | 12.71 |
| F/2 | EBG (0 min, 60 µL) | 214 | 13.84 | |
| F/1 | EBG (10 min, 60 µL) | 609 | 39.40 | 39.62 |
| F/2 | EBG (10 min, 60 µL) | 616 | 39.85 | |
| F/1 | EBG (20 min, 60 µL) | 629 | 40.69 | 43.47 |
| F/2 | EBG (20 min, 60 µL) | 715 | 46.25 | |
| 1 | IMCSzyme ™ (0 min, 60 µL) | 142 | 9.19 | 10.19 |
| 2 | IMCSzyme ™ (0 min, 60 µL) | 173 | 11.19 | |
| 1 | IMCSzyme ™ (10 min, 60 µL) | 603 | 39.01 | 39.20 |
| 2 | IMCSzyme ™ (10 min, 60 µL) | 609 | 39.40 | |
| 1 | IMCSzyme ™ (20 min, 60 µL) | 662 | 42.83 | 43.41 |
| 2 | IMCSzyme ™ (20 min, 60 µL) | 680 | 43.99 | |
| E/1 | Control (10 min) | No Peak | 0.00 | 0.00 |
| E/2 | Control (10 min) | No Peak | 0.00 | |

The invention claimed is:

1. A method for detecting opioids, opiates, cannabinoids, or benzodiazepines in a sample, comprising the steps of:
    (a) contacting the sample with an enzyme having β-glucuronidase activity, wherein the enzyme comprises an amino acid sequence having at least 99% sequence identity to SEQ ID NO:1 and is derived from *Brachyspira pilosicoli*, wherein the sample comprises glucuronide metabolites of opioids, opiates, cannabinoids, or benzodiazepines;
    (b) incubating the sample with the enzyme to produce opioids, opiates, cannabinoids, or benzodiazepines by hydrolysis or glycosidic bond cleavage of the glucuronide metabolites; and
    (c) detecting the opioids, opiates, cannabinoids, or benzodiazepines through any suitable technique.

2. The method of claim 1, wherein the sample is a biological sample.

3. The method of claim 2, wherein the biological sample is selected from the group consisting of saliva, whole blood, plasma, urine, hair, skin, teeth, soft tissues, meconium and vitreous humor.

4. The method of claim 1, wherein the step of incubating the sample with the enzyme is performed for a period between 1 and 30 minutes.

5. The method of claim 1, wherein the step of incubating the sample with the enzyme is performed at a temperature range between 20 and 60 degrees Celsius.

6. The method of claim 1, wherein the step of incubating the sample with the enzyme is performed at a range of pH between 4.0 and 9.0.

7. The method of claim 1, wherein the suitable technique for detecting the opioids, opiates, cannabinoids, or benzodiazepines is selected from the group consisting of LC-MS, GC-MS, HPLC-MS, LC-HRMS, HPLC-HRMS, LC-MS-MS, GC-MS-MS and HPLC-MS-MS.

* * * * *

SEQUENCE LISTING

```
Sequence total quantity: 3
SEQ ID NO: 1           moltype = AA   length = 603
FEATURE                Location/Qualifiers
source                 1..603
                       mol_type = protein
                       organism = Brachyspira pilosicoli
SEQUENCE: 1
MVNSMLYPRE SRTRRVVDIS GMWEFKIDIN NEGRNSGYAN GLKDTTFIPV PSSFNDLFTD  60
KNIREHAGDV WYETSFYLPL EWKDKDVNVR FGCATHEATV YINGKEVCTH VGGFMPFNAP 120
VNEAGIFGEK NKLVVVVNNE LSNTTIPCGH TETKPSGKKY IKPSFDFFNY AGLNRPVKIT 180
VTNKEYIHDI DILSDVNGSD GIVNYEVHTT GENKVYIKIN DEEGKEVASC EGKSGKIVIK 240
```

```
DAKLWNPKAA  YLYKFIACIK  NGDELIDEYY  LDFGIRTVKV  EGTKFLINGK  PFYFTGFGKH   300
EDSEIAGRGY  NPPVIKRDFE  LIKWVGANSF  RTSHYPYSEE  IMQAADREGI  VIIDEVAAVG   360
MFDVGSVLNP  SASKTDYFSL  DEVHSKTKEV  HKKAVEELIK  RDKNHPSVVM  WSLFNEPDTS   420
KDEAVPYFED  IFNFAKSQDK  QNLPKTFAAI  QASSPGKCKC  MHLCDVITLN  RYYGWYFLGG   480
YEIDMSEEKF  REEMNLYSNM  NKPVMFTEYG  ADTYAGVHKL  PSVMWSEEYQ  CEYYEMNFKV   540
FDSYDFIVGE  QLWNFADFQT  TEGIFRVDGN  KKGIFTRNRQ  PKAVAHLIRS  RWNKLPLDYK   600
SKK                                                                      603

SEQ ID NO: 2            moltype = DNA   length = 1809
FEATURE                 Location/Qualifiers
source                  1..1809
                        mol_type = genomic DNA
                        organism = Brachyspira pilosicoli
SEQUENCE: 2
atggttaatt ctatgttata tcctagagag agtaggacaa gaagagtagt agatatatct    60
ggtatgtggg agtttaaaat tgatataaat aatgaaggca gaaatagcgg atatgctaat   120
gggcttaaag atactacatt tatacctgtt ccatctagtt ttaatgattt atttacagat   180
aaaaatataa gagaacatgc tggtgatgta tggtatgaaa catcatttta tcttcctttg   240
gaatggaaag acaaagatgt taatgtaaga tttggttgtg caactcatga agctactgta   300
tatattaatg gaaagaagt atgtacacat gtaggtggat ttatgccttt caatgctcct   360
gtaaatgaag caggaatatt tggagaaaaa aataaattag ttgtagttgt taataatgaa   420
cttagcaata ctactatacc ttgtgtgtcat acagaaacta aaccttcagg caaaaaatat   480
attaaacctt cttttgactt ttttaattat gcgggattaa acagacctgt aaaaattact   540
gttacaaata aggaatatat acatgatata gatatattat cagatgtaaa cggcagtgat   600
ggaattgtaa attatgaagt acatactaca ggcgaaaaca aagtatatat aaaaataaac   660
gatgaagagg gaaaagaagt agcaagttgt gaaggtaaaa gcgggaaaat agttattaaa   720
gatgctaaat tatggaatcc aaaggctgct tatttgtata agttatttgc atgcataaaa   780
aatggcgatg aactcataga tgaatattat ttagacttg tataagaac tgttaaagtt   840
gaaggaacaa aattttttaat taatggaaaa cctttctact ttacaggatt tggtaaacat   900
gaagcagtg aaatagcagg taggggttat aatcctcctg taataaaaag agattttgag   960
ctcattaaat gggtaggtgc aaattcattt agaacatctc actatcctta tagtgaagaa  1020
ataatgcagg cagctgacag agaaggaatt gttattatag atgaagttgc tgctgtaggt  1080
atgtttgatg taggttctgt actaaatcct agtgcatcaa aaactgatta tttctcttta  1140
gatgaagtac atagcaaaac taagaagtt cataaaaaag ctgttgaaga gcttattaaa  1200
agagataaaa atcaccccttc agttgttatg tggagtttat tcaatgagcc tgatacttca  1260
aaagacgaag ctgttccata ttttgaagat atattaatt ttgctaaag tcaggataag  1320
cagaatcttc ctaaaacttt tgctgctatt caggcatctt ctcctggaaa atgtaagtgt  1380
atgcatttat gcgatgtaa tacattaat agatactatg gatggtattt cttgggtggt  1440
tatgaaattg atatgtcaga agaaaaattt agagaagaaa tgaatttgta ttctaatatg  1500
aataaaccag ttatgttcac agaatacgga gctgatactt atgctggtgt tcataaactt  1560
ccttccgtaa tgtggagcga agaatatcaa tgcgaatact atgaaatgaa tttcaaagtt  1620
tttgatagct atgactttat agttggagaa caattatgga actttgctga ttttcaaact  1680
actgaaggaa tatttagggt agatggaaat aaaaaaggta tatttactag aaaccgtcag  1740
cctaaagccg ttgctcatct tataagaagc agatggaata agttgccatt agattataaa  1800
tcaaaaaaa                                                           1809

SEQ ID NO: 3            moltype = DNA   length = 1823
FEATURE                 Location/Qualifiers
misc_feature            1..1823
                        note = Sequence optimized for its expression in E. coli
source                  1..1823
                        mol_type = other DNA
                        organism = synthetic construct
SEQUENCE: 3
ccatgggcat ggtcaatagt atgctgtatc cgcgtgaaag ccgcaccgc cgtgttgtgg    60
acatctctgg catgtgggaa ttcaaaatcg acatcaacaa tgaaggccgt aacagtggtt   120
atgcgaatgg cctgaaagat accacgtttt ttccggtccc gagctctttt aacgaccgt   180
ttaccgacaa aaatatccgt gaacatgccg gtgatgtttg gtatgaaacg agcttctacc   240
tgccgctgga atggaaagat aaagacgtga acgttcgctt tggttgcgcg acccatgaag   300
ccacggtgta tattaatggc aaagaagtct gtacccacgt gggcggtttt atgccgttta   360
acgcgccggt taatgaagcc ggcatctttcg gcgagaaaaa caaactggtg gttgtctgtga  420
acaatgaact gtccaatacc acgattccgt gcggtcacac cgaaacgaaa ccgagcggca   480
aaaatatcat caaaccgtct tttgatttct taactacgc aggcctgaat cgtccggtta   540
aaatcaccgt cacgaacaaa gaatacatcc atgatatcga tatcctgtca gatgtgaacg   600
gctcggacgg tattgtgaat tatgaagttc acaccacggg tgaaaacaaa gtttacatca   660
aaatcaacga tgaagaaggc aaagaagtcg cgagctgcga aggcaaatct ggtaaaattg   720
tgatcaaaga tgccaaactg tggaacccga agcggcccta cctgtacaaa ttcatcgcct   780
gtatcaaaaa cggtgatgaa ctgattgacg aatattacct ggattttggc atccgcaccg   840
tcaaagtgga gggtacgaaa ttcctgatta acggcaaacc gttttatttc accggcttta   900
gtaaacatga agattctgaa atcgcaggcc gtggttacaa cccgcccggtt attaacgcg   960
actttgaact gatcaaatgg gtcggtgcta atagcttccg tacctctcac tatccgtaca  1020
gcgaagaaat tatgcaggca gctgatcgcg aaggcatcgt gattatcgac gaagttgcgg  1080
ccgtcggcat gttcgatgtg ggctctgttc tgaatccgtc agcgtcgaaa accgattatt  1140
tttcactgga cgaagttcat tcgaaaacga aagaagtca caagaaagcg gtggaagaac  1200
tgattaaacg tgataaaaac catccgagtg ttgtcatgtg gtccctgttc aatgaaccgg  1260
atacctcaaa agacgaagca gtgccgtact cgaagatat cttcaacttc gctaaatcgc  1320
aggacaaaca aaatctgccg aaaacctttg cagctatcca ggcgagttcc ccgggtaaat  1380
gcaaatgtat gcatctgtgc gatgtgatta cgctgaaccg ttattacggc tggtatttcc  1440
tgggcggtta cgaaatcgac atgagtgaag aaaaattccg cgaagaaatg aacctgtact  1500
```

```
ccaacatgaa caaaccggtt atgttcaccg aatatggtgc agatacgtac gctggcgttc 1560
acaaactgcc gagtgtcatg tggtccgaag aataccagtg tgaatactac gaaatgaact 1620
tcaaagtgtt cgatagctac gactttattg ttggtgaaca gctgtggaat tttgcagatt 1680
tccaaaccac ggaaggcatt tttcgcgtgg acggtaacaa gaaaggcatc ttcacccgta 1740
atcgccaacc gaaagctgtc gcacatctga ttcgctcccg ttggaacaaa ctgccgctgg 1800
actacaaaag taagaagaag ctt                                        1823
```